United States Patent
Seethapathy et al.

(10) Patent No.: US 10,275,552 B2
(45) Date of Patent: Apr. 30, 2019

(54) METHOD OF DETERMINING WAVE PROPAGATION IN A MEDIUM

(71) Applicant: ROLLS-ROYCE PLC, London (GB)

(72) Inventors: Mani Seethapathy, Derby (GB); Sree Vamsi Tammineni, Wilmslow (GB); Stephen Samuel Wiseall, Derby (GB); David Cameron Wright, Loughborough (GB); Craig Brian Chapman, Manchester (GB); Pathmeswaran Raju, New Malden (GB)

(73) Assignee: ROLLS-ROYCE plc, London (GB)

(*) Notice: Subject to any disclaimer, the term of this patent is extended or adjusted under 35 U.S.C. 154(b) by 412 days.

(21) Appl. No.: 14/932,531

(22) Filed: Nov. 4, 2015

(65) Prior Publication Data

US 2016/0140270 A1 May 19, 2016

(30) Foreign Application Priority Data

Nov. 18, 2014 (GB) .................................. 1420425.9

(51) Int. Cl.
*G01N 29/44* (2006.01)
*G06F 17/50* (2006.01)

(52) U.S. Cl.
CPC ..... *G06F 17/5018* (2013.01); *G01N 29/4472* (2013.01); *G06F 2217/14* (2013.01)

(58) Field of Classification Search
CPC ......................... G01N 29/4472; G06F 2217/14
See application file for complete search history.

(56) References Cited

U.S. PATENT DOCUMENTS

| 8,965,100 B2* | 2/2015 | Lin ..................... G01N 29/4472 382/141 |
| 9,152,744 B2* | 10/2015 | Grellou ............... G06F 17/5009 |
| 2005/0139006 A1* | 6/2005 | Lorraine .............. G01N 29/043 73/597 |

(Continued)

OTHER PUBLICATIONS

Garton, M., et al. "UTSIM: Overview and Application" AIP Conf. Proc., 1211, 2141 (2010) (Year: 2010).*

(Continued)

*Primary Examiner* — Jay Hann
(74) *Attorney, Agent, or Firm* — Oliff PLC

(57) ABSTRACT

A method including the steps of: defining an original parent polygon representative domain of interest, an origin corresponding to a wavesource position within the parent, a wavesource wavefront geometry, and a maximum wavefront extent; determining one or more valid parent polygon sides; defining cutting lines from the vertices of each valid parent side to the extent; reflecting the parent about the respective valid side defining a child polygon; discarding portions of each child polygon lying beyond a cutting line from the respective parent side; redefining each child as a parent, and repeating the second to fifth steps for each parent filling the area within the extent; projecting onto the polygons within the extent, a wavefront having the wavefront geometry spaced from the origin by a specified distance; and reflecting the child polygons along the respective sides of their respective parents projecting the child polygons and wavefront onto the original parent.

13 Claims, 14 Drawing Sheets

(56) References Cited

U.S. PATENT DOCUMENTS

2014/0278292 A1* 9/2014 Grellou ............... G01N 29/265 703/2
2016/0139087 A1* 5/2016 Seethapathy ...... G01N 29/4472 702/39

OTHER PUBLICATIONS

Shan, H., et al. "The Developments of Simulation Software for Ultrasonic Testing" 17th World Conf. on Nondestructive Testing (Oct. 2008) (Year: 2008).*
Garton, M. "Refining Automated Ultrasonic Inspections with Simulation Models" Review of Progress in Quantitative Nondestructive Evaluation, vol. 17 (1998) (Year: 1998).*
Yamawaki et al., "Numerical Calculation of Ultrasonic Propagation with Antisotropy", NDT & E International, vol. 33, Issued 7, 2000, pp. 489-497.
Mares, "Simulation as a Support for Ultrasonic Testing", Journal of Modern Physics, 2014, pp. 1167-1172.
Jun. 3, 2015 Search Report issued in British Patent Application No. 1420425.9.
Drumm et al., "The Adaptive Beam-Tracing Algorithm", J. Acoust. Soc. Am. vol. 107, 2000, pp. 1405-1412.
Allen et al., "Image Method for Efficiently Simulating Small-Room Acoustics", J. Acoust. Soc. Am., vol. 64, 1979, pp. 943-950.
Alpkocak et al., "Computing Impulse Response of Room Acoustics Using the Ray-Tracing Method in Time Domain", Archives of Acoustics, vol. 35., 2010, pp. 505-519.
Ogilvy et al., "Ultrasonic Beam Profiles and Beam Propagation in an Ustenitic Weld Using a Theoretical Ray Tracing Model", Ultrasonics, IPC Science and Technology Press Ltd., vol. 24, 1986.
Yamawaki H. et al., "Numerical Calculation of Ultrasonic Propagation with Anisotropy", NDT & E International, Butterworth-Heinemann, Oxford, vol. 33, 2000.
Jun. 3, 2016 Search Report issued in European Patent Application No. 15192519.

* cited by examiner

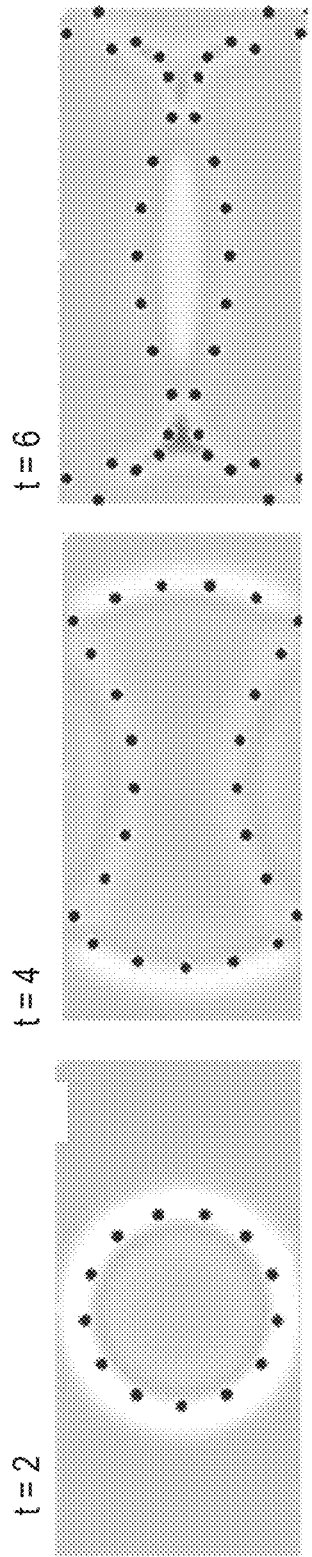
FIG. 9a  t=2
FIG. 9b  t=4
FIG. 9c  t=6
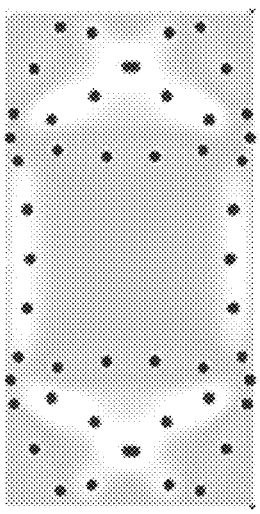
FIG. 9d  t=8
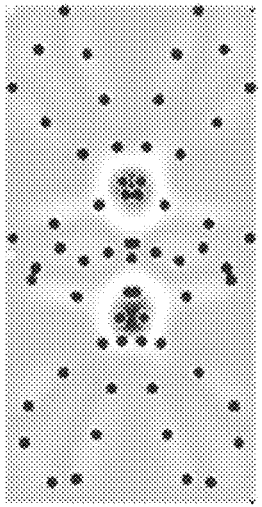
FIG. 9e  t=10

METHOD OF DETERMINING WAVE PROPAGATION IN A MEDIUM

FIELD OF THE INVENTION

The present invention relates to a method of determining wave propagation in a medium, and particularly but not exclusively to a method of determining ultrasound propagation through a candidate metallic preform shape to determine whether the metallic preform shape is inspectable by ultrasonic testing.

BACKGROUND TO THE INVENTION

Waves such as electromagnetic, seismic and acoustic waves propagate through media in a predictable way in accordance with well understood physical principles. However, directly determining wave propagation through a medium having complex boundaries in accordance with physical laws is computationally expensive.

In one example, it may be desirable to perform non-destructive testing (NDT) in the form of ultrasonic testing on a workpiece to ensure that no defects such as inclusions are present in the raw material prior to carrying out further machining. FIG. 1 shows a cross sectional view through part of a forging 10 for a turbine disc of a gas turbine engine. The turbine disc is annular, having a shape shown in FIG. 2. The forging 10 includes an initial workpiece profile 12 (also known as a "Condition of Supply", or COS) which is machined from a larger casting geometry 11. The workpiece 12 comprises a polygon having rectilinear sides. The workpiece 12 is further machined to form a final profile 14, which is the required shape of the turbine disc. Before the workpiece 12 is further machined, the workpiece 12 is placed within an ultrasonic inspection apparatus 15 shown in FIG. 2. The apparatus 15 contains sound conducting media such as water 16 which has a different refractive index than the workpiece 12 due to the lower speed of sound in water. An ultrasonic transducer 18 is used to perform ultrasonic testing on the workpiece 12 to determine whether parts of the final profile 14 which will be subject to high stresses include any defects.

In order to inspect the workpiece 12 to the satisfaction of regulatory authorities, it must be shown that the final profile 14 can be subjected to three separate ultrasonic testing passes per side of the workpiece profile 12. When designing the workpiece profile 12 therefore, NDT requirements require that the final profile 14 can be tested from angles defined by the external profile of the workpiece 12.

Methods are known for simulating wave propagation in order to, for instance, model ultrasonic testing of an article. On a physical level, wave propagation is governed by a wave equation, which is a partial differential equation. Methods for solving this equation to simulate wave propagation across a domain of interest over time include methods such as the Finite Difference Method (FDM), the Finite Element Method (FEM). FDM and FEM are known as "meshed" methods, and operate by discretising the problem domain into a plurality of sub-domains (or cells) known as a mesh. In the case of FDM, the differential operators in the wave equations are replaced with the difference approximations from the Taylor series. A further wave based method comprises the Boundary Element Method (BEM).

"Meshless" methods are also known, such as the Distributed Point Source Method (DPSM). In this method, the transducer face and interfaces are modelled as distributed point sources. The field variables of the ultrasonic wave are computed using Green's function. Based on Green's function, an arbitrary point in space will be influenced by the distributed points surrounded by it. Mesh free methods are preferable in some situations to meshed methods, as they have high computational efficiency. One type of Meshless method is known as a "Domain type" method. In Domain type methods, the differential equations are approximated at the boundary as well as in the domain. Strong or weak formulations of the wave equation are used in the domain area, as this type of solution is well behaved in the domain. However, in known methods, singularities (i.e. computational errors) occur at boundaries as well as at defect areas, making it difficult to distinguish boundaries from defects in the model.

Another method of solving partial differential equations such as wave equations is known as "Particle-in-Cell" (PIC). In this method, individual particles representative of field variables of the wave front are tracked in continuous phase space in a Langrangian frame, whereas the equations of motion are integrated in a computational grid known as a cell. The particles do not interact (i.e. collide) with each other. The main disadvantage of PIC is that it is computationally expensive due to the large background mesh. Increasing the size of the cells will result in faster computation, but will also result in a solution having lower accuracy. This is due to the bi-directional computation between the cell and particle layers, wherein the cell properties are calculated in part from the results of the particle layer from the previous time step, and vice versa.

In each case there is therefore a compromise between wave propagation simulation accuracy and computational expense, as more accuracy generally leads to longer computational time required to carry out the calculation. Other methods include geometrical methods such as ray tracing (described in Alpkocak and Sis, 2010), the Image Source Method (ISM, described in (Allen and Berkley, 1979) and beam tracing (described in Drumm and Lam, 2000). However, while faster, such geometrical methods are less accurate.

Consequently, there is a desire to provide a new method of determining wave propagation through media such as metals in order to, for example, determine the available scan coverage of an article. Such a method must be computationally efficient, as well as highly accurate. The present invention seeks to provide such a method.

SUMMARY OF THE INVENTION

According to a first aspect of the present invention, there is provided a computer implemented method of determining propagation of an energy wave with respect to time through a domain of interest, the method comprising the steps of:
(1) defining: an original parent polygon (D) representative of the domain of interest; an origin (SE) corresponding to a position of a wavesource within the parent polygon (D); a wavefront geometry of the wavesource; and a maximum wavefront extent (R);
(2) determining one or more valid polygon sides (E) of the parent polygon;
(3) for each valid side (E) of the parent polygon (D), defining a plurality of cutting lines (CL) extending from the vertices (V) of the valid sides (E) to the maximum wavefront extent (R);
(4) for each valid side (E) of the parent polygon (D), reflecting the parent polygon (D) about the respective side (E) to define a child polygon ($D_n$);

(5) discarding portions of each child polygon ($D_n$) which lies beyond a cutting line (CL) from the respective side (E) of the parent polygon (D);

(6) redefining each child polygon ($D_n$) as a parent polygon (D), and repeating steps (2) to (5) for each parent polygon (D) until the area within the maximum wavefront extent (R) is filled with polygons ($D_n$);

(7) projecting onto the polygons (D, $D_n$) within the maximum wavefront extent (R), a wavefront (WF) having the wavefront geometry spaced from the origin (SE) by a specified distance (X); and (8) reflecting the child polygons ($D_n$) along the respective sides (E) of their respective parent polygons (D) to project the child polygons ($D_n$) and wavefront (WF) onto the original parent polygon (D).

Accordingly, the invention provides a method of determining wave propagation though a domain of interest, by calculating wave reflections using an origami map formed by reflections of the test polygon about valid sides. By projecting a wavefront onto the origami map, then refolding the map and wavefront onto the original test polygon, reflections of the wave from the sides of the original parent polygon can be efficiently modelled. The method is particularly suitable for modelling acoustic wavefronts in ultrasound testing.

The original parent polygon (D) may have a geometry representative of a nominal geometry of a workpiece to be inspected by ultrasonic testing.

The wavefront geometry may comprise one of a circular wavefront geometry, a spherical wavefront geometry, a linear wavefront geometry and a planar wavefront geometry.

The step of defining the maximum extent of the wavefront (R) of the predetermined time limit may comprise calculating the maximum distance ($X_R$) of the wavefront (WF) from the origin (SE) at the predetermined time using the formula:

$$X_R = cT$$

Where c is the speed of propagation of the wave and T is a predetermined maximum wavefront propagation time. Where the wavefront geometry is circular, the maximum extent (R) may comprise a circle centred on the origin having a radius ($X_R$), where the wavefront geometry is spherical, the maximum extent may comprise a sphere centred on the origin having a radius ($X_R$), where the wavefront geometry is linear, the maximum extent may comprise a line located at a distance ($X_R$) from the origin, and where the wavefront geometry is planar, the maximum extent may comprise a plane located at a distance ($X_R$) from the origin.

Where the wavefront geometry comprises a circular or spherical wavefront geometry, the step of determining one or more valid polygon sides (E) may comprise, for each side (E) of the parent polygon (D), defining a pair of cutting lines (CL) extending from the origin (SE) to the vertices (V) of the respective side (E), wherein the respective polygon side (E) is deemed not to be visible from the origin (SE) where either of the pair of cutting lines (CL) extends through a different side (E) of the polygon prior to reaching the respective side (E) of the respective parent polygon (D).

Where the wavefront geometry comprises a linear or planar geometry, the step of determining one or more valid polygon sides (E) may comprise defining an initial wavefront vector ($SE_V$) and, for each side (E) of the parent polygon (D), projecting a cutting line (CL) from the vertices (V) of each side (E) in the direction of the initial wavefront vector ($SE_V$), and determining whether the cutting lines (CL) extend toward the interior of the parent polygon (D), wherein the respective polygon side (E) is deemed not to be visible where either cutting line (CL) of the respective side (E) extends toward the interior of the parent polygon (D).

Where the wavefront geometry comprises a circular or spherical wavefront geometry, the step of defining a plurality of cutting lines (CL) comprises projecting respective cutting lines (CL) from the origin (SE) through the vertices (V) of each valid side (E), to the wavefront maximum extent (R).

Where the wavefront geometry comprises a linear or planar wavefront geometry, the step of defining a plurality of cutting lines (CL) comprises projecting respective cutting lines (CL) from the vertices (V) of the valid sides (E) toward the wavefront maximum extent (R) in the direction of the initial wavefront vector ($SE_V$).

The energy wave may comprise one of an acoustic wave such as an ultrasonic wave, an electromagnetic wave and a seismic wave. The acoustic wave type may comprise one or more of a longitudinal waves, Sholte wave (interface waves), Rayleigh wave, shear wave, Stonley waves and Love wave.

The step of defining the wavefront (WF) may comprise discretising the wave front (WF) into a plurality of spaced master particles, each master particle representing the position and field variables of a portion of the wavefront (WF) at the location of the respective master particle.

The step of projecting the wavefront (WF) onto the reflected polygons ($D_n$) may comprise assigning each master particle to the respective polygon ($D_n$) having the nearest centroid.

The method may comprise defining a supporting domain $\Omega_m$ for each master particle; computing field variables including the position, magnitude and direction of propagation of each master particle at a required time step; defining a plurality of virtual particles spaced within the domain representative of the magnitude of a field variable of the wave at the location of the respective virtual particle; calculating a magnitude $u_v$ of the field variable of each virtual particle at the time of interest by applying the formula:

$$u_v = \sum_{m=1}^{N} u_m f(q1) \times g(q2)$$

Where N is the number of master particles within whose supporting domain $\Omega_m$ the respective virtual particle is located, $u_m$ is the magnitude of a respective master particle, $f(q1)$ is an envelope function relating the magnitude of the virtual particle to the distance from the master particle in the direction of propagation of the master particle, and $g(q2)$ is a smoothing function relating the magnitude of the virtual particle to the distance from the master particle normal to the direction of propagation of the master particle.

The supporting domain may comprise an ellipse having a first axis (q1) in the direction of propagation of the master particle, and a second axis (q2) in a direction normal to the propagation of the master particle. The length of the first axis q1 may comprise the wavelength of the energy wave, or may comprise the pulse length of the energy wave. The length of the second axis q2 may comprise the distance between master particles in the domain.

Each of the envelope function and the smoothing function may comprise a Gaussian function.

According to a second aspect of the invention, there is provided a data carrier comprising machine readable instructions for the operation of one or more processors to perform the method of the first aspect of the present invention.

According to a third aspect of the invention there is provided a method of determining the inspectability of a component by ultrasonic testing, the method comprising the steps of:
defining a geometry representative of the component to be inspected, the geometry comprising one or more critical regions;
simulating wavefront propagation from a first side of the geometry to a second side in accordance with the first aspect of the invention;
wherein the second side is determined to be inspectable from the first side where the wavefront is reflected back to the first side from the second time within a predetermined maximum propagation time.

Advantageously, the method of the present disclosure can be used to determine the inspectability of a component in a computationally efficient and accurate manner. Consequently, the time taken for designing the component is reduced, and redesigns due to simulation inaccuracies are also reduced.

According to a fourth aspect of the invention there is provided a design method comprising:
defining a first candidate component geometry;
using a method in accordance with the third aspect of the invention to determine the inspectability of the candidate component geometry;
providing one or more further candidate design geometries on the basis of the results of the inspectability test.

BRIEF DESCRIPTION OF THE DRAWINGS

FIGS. 9a to 9e show visualisations of wavefront propagation determined in accordance with the method of the present disclosure.

DETAILED DESCRIPTION

Figure 1:
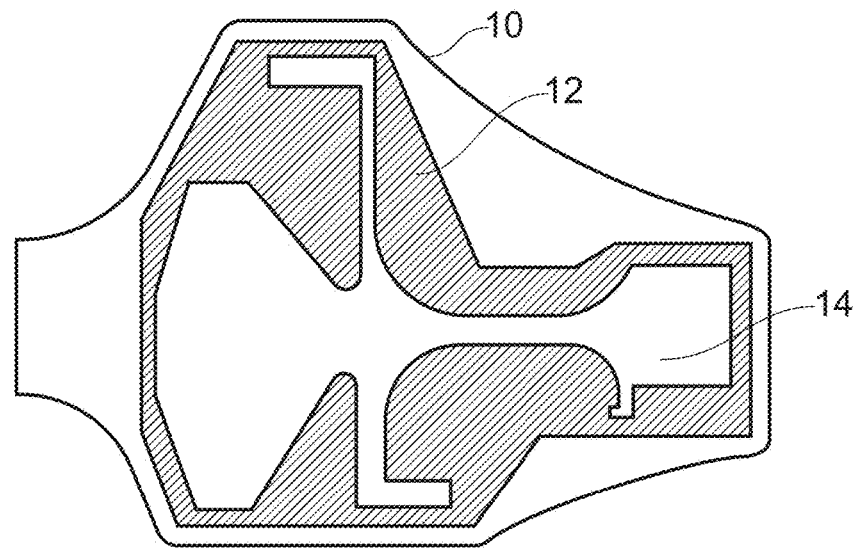
FIG. 1 shows a cross sectional view through a casting suitable for producing a rotor disc of a gas turbine engine.

FIG. 1 shows a cross sectional view through a casting 10 suitable for producing a rotor disc 14 of a gas turbine engine (not shown). The casting 10 includes a Condition of Supply (COS) 12 within the casting 10, which is to be inspected by a non-destructive ultrasonic evaluation method using the apparatus shown in FIG. 2.

The COS 12 must meet several requirements:
1. The COS 12 must encompass the entirety of the rotor disc 14.
2. At least critical regions of the COS 12 such as regions of the rotor disc 14 subject to high stress levels in use must be inspectable from at least three different positions on the external surface of the COS 12.
3. The COS 12 must use a minimum amount of material in order to minimise manufacturing costs.

Figure 3:
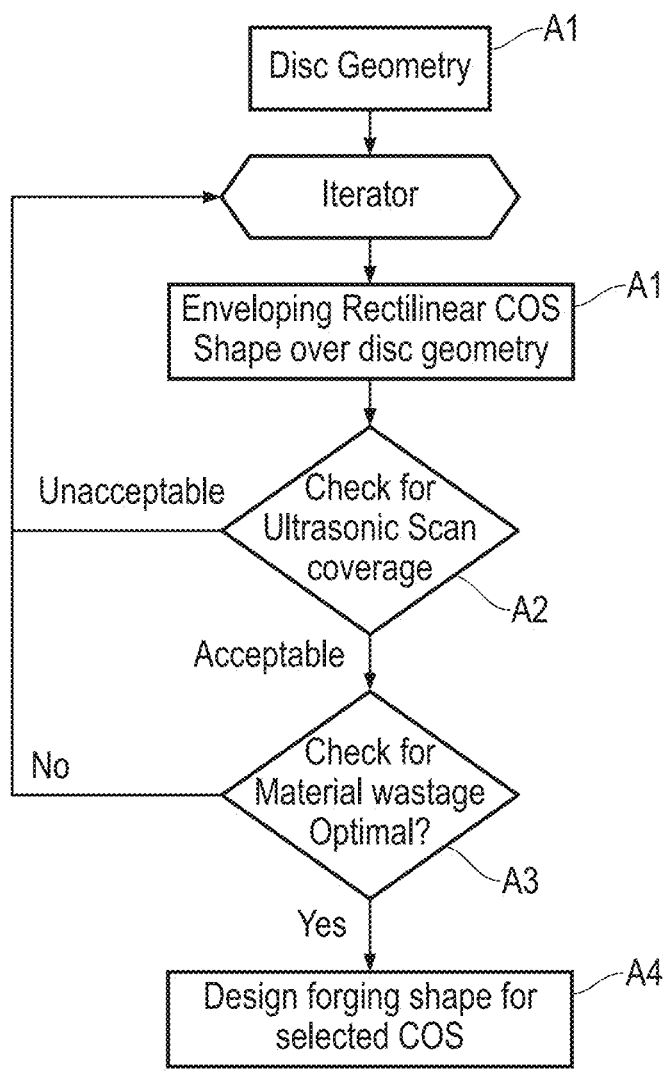
FIG. 3 shows a flow diagram illustrating a method in accordance with the present disclosure.

Consequently, the COS 12 is designed in accordance with an iterative design method in accordance with the present disclosure, as outlined in FIG. 3.

In a first step A1 of the design method, an initial candidate COS geometry is defined, which satisfies the requirement that the COS 12 encompasses the entirety of the disc 14. In a second step A2, a computerised ultrasonic testing simulation method ("scan plan") is performed on the candidate geometry to determine whether all critical regions of the candidate COS 12 are inspectable from at least three positions on the external surface of the COS 12 (i.e. from three different external sides of the polygonal geometry). If the candidate geometry is not inspectable from at least three positions, the process returns to step A1, and the COS 12 is redesigned to produce an iterated candidate geometry. Optionally, if the candidate COS geometry is found to satisfy the inspectability requirements, the candidate COS 12 may be subjected to a material use optimisation test in step A3. If the material usage is found to be acceptable, a forging shape 10 is designed in step A4, which encompasses the COS 12 and satisfies the shape restraints of the forging process.

Figure 4:
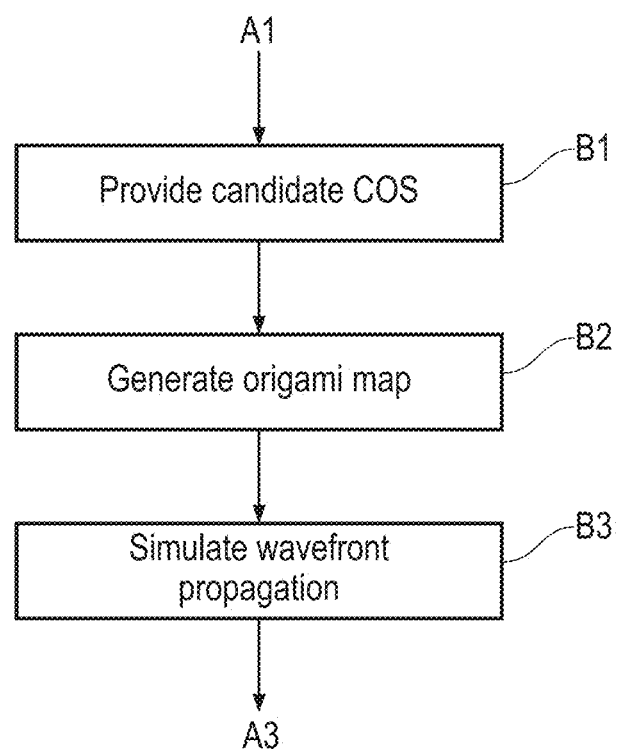
FIG. 4 shows a flow diagram of step A2 of the method of FIG. 3.
Figure 5:
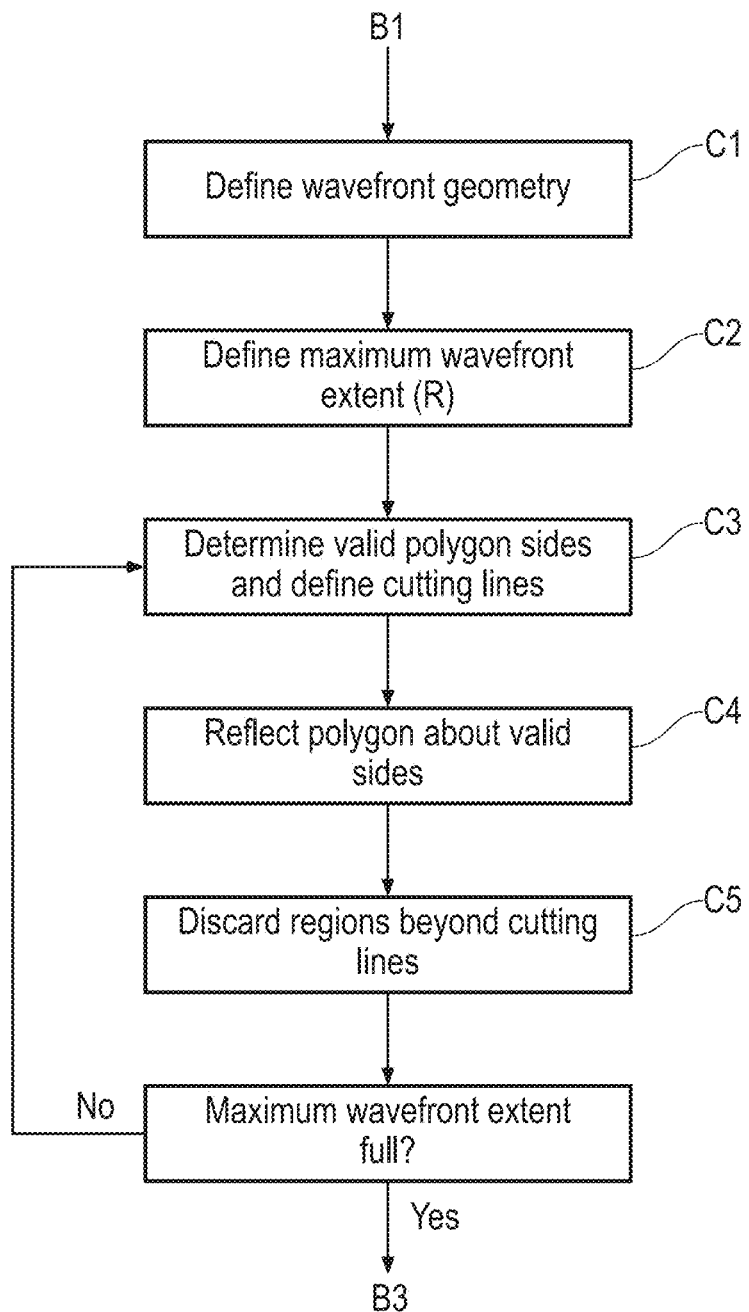
FIG. 5 shows a flow diagram of step B2 of the step A2.
Figure 6:
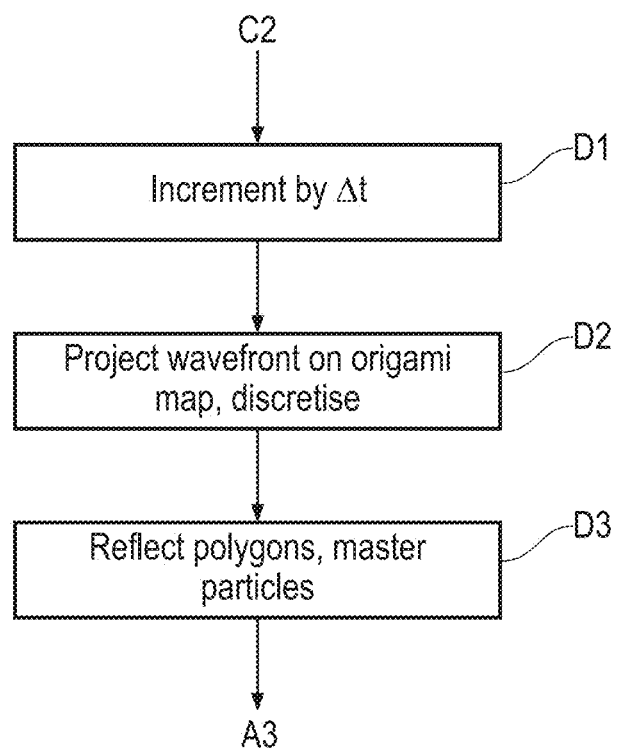
FIG. 6 shows a flow diagram of step B3.

FIG. 4 shows ultrasonic testing simulation method step A2 in more detail. In a first sub-step B1, the candidate COS 12 is provided as a candidate original parent polygon D, along with a candidate wave origin location SE within or on a surface of the candidate parent polygon D. The origin SE is chosen to correspond to the location of a wavesource, such as a potential placement location of a transducer 18. The candidate polygon D has a polygonal geometry, and may be either two dimensional or three dimensional. To aid clarity, in the following examples, a four sided two dimensional candidate original parent polygon D is described, wherein the sides are labelled 1, 2, 3, 4 in a clockwise direction. Of course, the method is suitable for polygons having three or more sides, and also to three dimensional polygons.

Optionally, the method may comprise two separate layers—a computational layer which calculates the position and field variables such as magnitude and direction of propagation of a portion of a simulated wave at a required time step $\Delta t$, and a visualisation layer, which calculates superpositions of the wavefronts, and provides a representation of the magnitude of the wavefront at the time step $\Delta t$.

In a second sub-step B2, an origami map is produced for the candidate COS 12. The origami map is to be used to simulate wave propagation from the origin SE to a maximum wavefront extent R through the candidate COS 12 in the computational layer.

The production of the origami map comprises performing a plurality of sub-steps. In sub step C1, a wavefront geometry is defined. The wavefront geometry is chosen to closely represent the geometry of the wavefront of the wave being simulated. Typically, where the simulation is two dimensional, the wavefront is either circular or linear, whereas the wavefront may be spherical or planar in the three dimensional case. A circular or spherical wavefront is typically selected where the wavesource is a closely located point source, whereas a linear or planar wavefront is typically selected where the wavesource is a distantly located point source, or originates from a densely packed array.

Figure 7A:
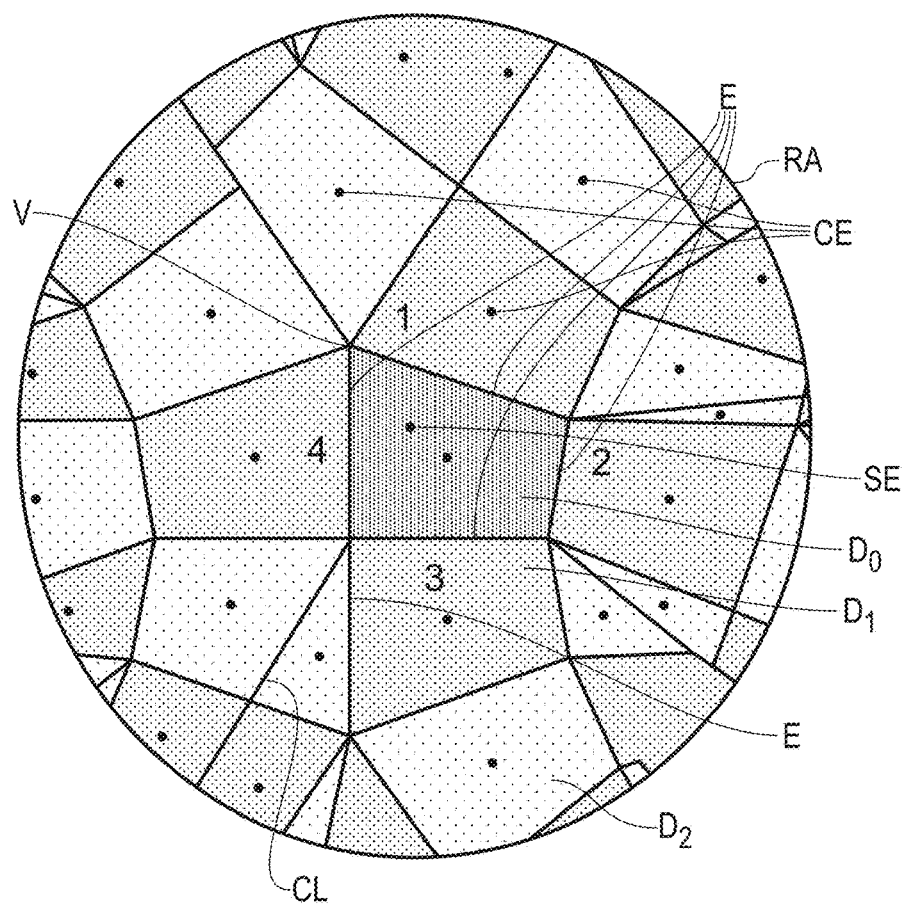
FIGS. 7a and 7b show an origami map generated by step B2 for a circular wavefront and a linear wavefront respectively.
Figure 7B:
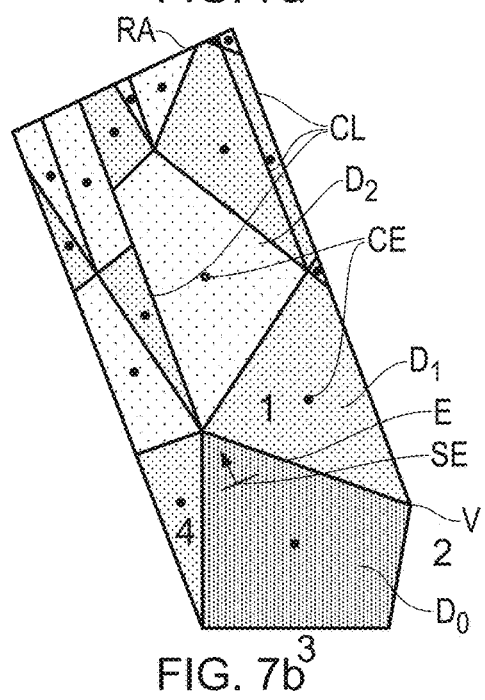

In substep C2, the maximum extent R of the wavefront is determined. The maximum extent R defines the area of the origami map. Where the wavefront is circular/spherical, the maximum extent R comprises a circle/sphere circle centred on the origin SE and having a radius x (see FIG. 7a). The radius x is calculated in accordance with the following formula:

$$x = cT \quad \text{(equation 1)}$$

Where the wavefront is linear/planar, the maximum extent RA comprises a line/plane located at a distance x from the origin SE (see FIG. 7b). Again, the distance x is calculated in accordance with equation 1. In each case, T may be chosen in accordance with a predicted or estimated time of absorption ratio and/or attenuation ratio of the material under investigation, such that, at time T, the wave has attenuated to the point where it can no longer be detected by the array being modelled.

In sub-step C3, valid polygon sides E for further processing are determined. For a circular or spherical wavefront, valid polygon sides E are those that are entirely visible from the origin SE, whereas for a linear/planar wavefront, valid sides E are those that at least partly lie in the path of the initial wavefront vector from the origin SE. Consequently, valid polygon sides E are determined using methods according to whether the wavefront geometry is circular/spherical, or linear/planar.

Where the wavefront is circular/spherical, the method comprises defining a pair of cutting lines CL, extending from the origin SE to the vertices V of the respective side 1, 2, 3, 4. The respective polygon side E is deemed not to be visible from the origin SE (and so to be invalid) where either of the pair of cutting lines CL extends through another side E of the parent polygon D prior to reaching the respective side E under consideration of the parent polygon D. This may be the case for instance where one of the vertices of the respective side the polygon comprises a concave external angle such that both vertices V of the side E under investigation are not visible from the origin SE.

Where the wavefront is linear/planar, the method comprises defining an initial wavefront vector $SE_V$ and, for each side 1, 2, 3, 4 of the polygon D, projecting a cutting line CL from the vertices V of each side 1, 2, 3, 4 to the maximum wavefront extent RA. The initial wavefront vector $SE_V$ is defined to represent the initial direction of travel of the wavefront from the origin SE. The respective polygon side 1, 2, 3, 4 is deemed to be invalid where either notional line CL of the respective side 1, 2, 3, 4 extends toward the interior of the parent polygon D, as is the case for sides 2 and 3 in the example shown.

In sub-step C4 the polygon D is reflected about each of the valid sides 1, 2, 3, 4. These reflected polygons $D_n$ ($D_1$ and $D_2$ are shown in FIGS. 7a and 7b) are termed child polygons $D_n$. The first child polygons are termed first order reflections, and are labelled $D_1$ hereafter. In this step, a centroid A representing the geometric centre of the respective reflected polygon $D_1$ is defined. The centroid A can be calculated by finding the arithmetic mean of all the vertices V of the polygon D.

In sub-step C5, portions of each reflected polygon $D_1$ which lies beyond a cutting line CL from the respective side (E) of the parent polygon (D) are discarded. The remaining area of the reflected polygons $D_1$ defines an "origami space".

Each child polygon $D_n$ is then redefined as a new parent polygon D. Steps B2c to B2e are then repeated for each new parent polygon $D_1$ to form second order reflected polygons $D_2$. Steps B2c to B2f are then continually repeated to form $n^{th}$ order polygons $D_n$, until the area within the maximum wavefront extent R is filled with reflected polygons $D_n$. The origami map stage is thus completed.

The next sub-step B3 then uses the generated origami map to simulate wavefront propagation over time from the wavesource location SE. This sub-step comprises a number of further sub-steps.

Figure 8A:
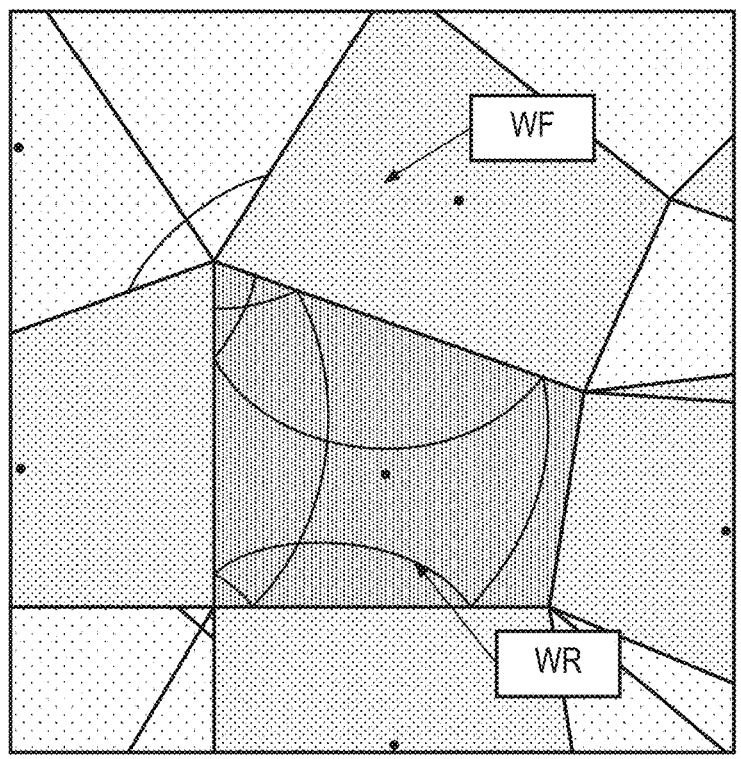
FIGS. 8a and 8b show a simulation step B3 using the origami map of FIG. 7a and FIG. 8b respectively.
Figure 8B:
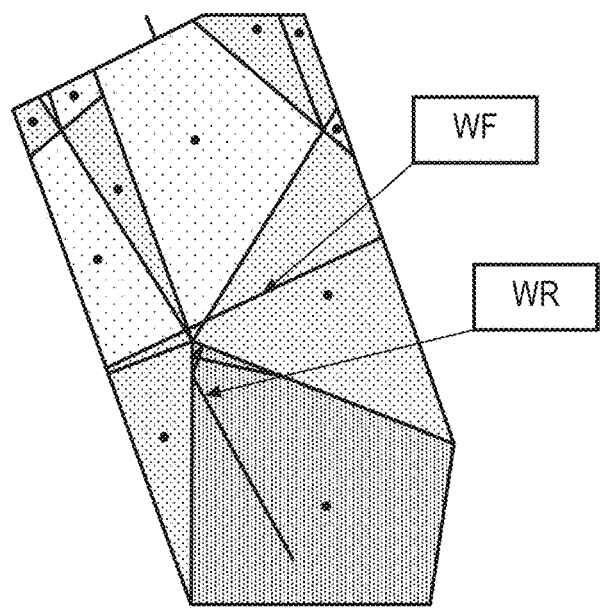

In a sub-step D1, a desired time step Δt is applied to the simulation. The desired time step would be chosen in accordance with a desired temporal resolution of the simulation. The wavefront is advanced from the origin a distance x in accordance with an assigned velocity c of the wave under investigation, in accordance with equation 1. Where the wavefront is circular, a test wavefront WF comprising a circle having a diameter x centred on the origin SE is projected onto the origami space, whereas where the wavefront is linear, a test wavefront WF comprising a line is projected onto the origami map a distance x in the direction of the initial wavefront vector $SE_V$ (see FIGS. 8a and 8b respectively).

Optionally, in step D2, the wavefront may be discretised into master particles 22 spaced along the wavefront. The master particles inherit the magnitude, location and direction of propagation of the wavefront at the respective location of each master particles 22. In step B3c, each master particle 22 is assigned a reflected $D_n$ polygon in accordance with the polygon $D_n$ having the nearest centroid to that master particle 22. Alternatively, the wavefront may be directly represented within software as a continuous smooth curve.

In step D3, the reflected polygons $D_n$ and projected wavefront WF are reflected back in order to project the reflected polygons $D_n$ and test wavefront onto the original test polygon D. The master particles 22 are also reflected, and so their location and direction of propagation is reflected accordingly.

The reflections are performed in reverse order of the reflected polygon order numbers $D_n$, so that polygon $D_n$ is reflected onto its parent, $D_{n-1}$, via the side E of the parent which created that respective reflected polygon $D_n$, $Dn_{-1}$ is reflected onto its parent $D_{n-2}$ etc.

By virtues of reflecting all the reflected polygons $D_n$ are reflected back such that all the polygons overlie the original parent polygon D, a folded wavefront pattern WR is defined, as shown in FIG. 8. This represents the wavefront extent at the selected time step Δt, if the wavefront had been reflected by the valid sides E of the original parent polygon D. Consequently, the above described method allows wavefront propagation to be simulated. This itself is a useful output, as it can be seen through which parts of the original parent polygon the wavefront has passed.

FIG. 3 shows steps in a more complete method of simulating propagation and resultant wavefront characteristics such as field variables of an energy wave through a medium with respect to time in accordance with the present disclosure. Example results of this simulation are shown in FIG. 9.

Figure 10:
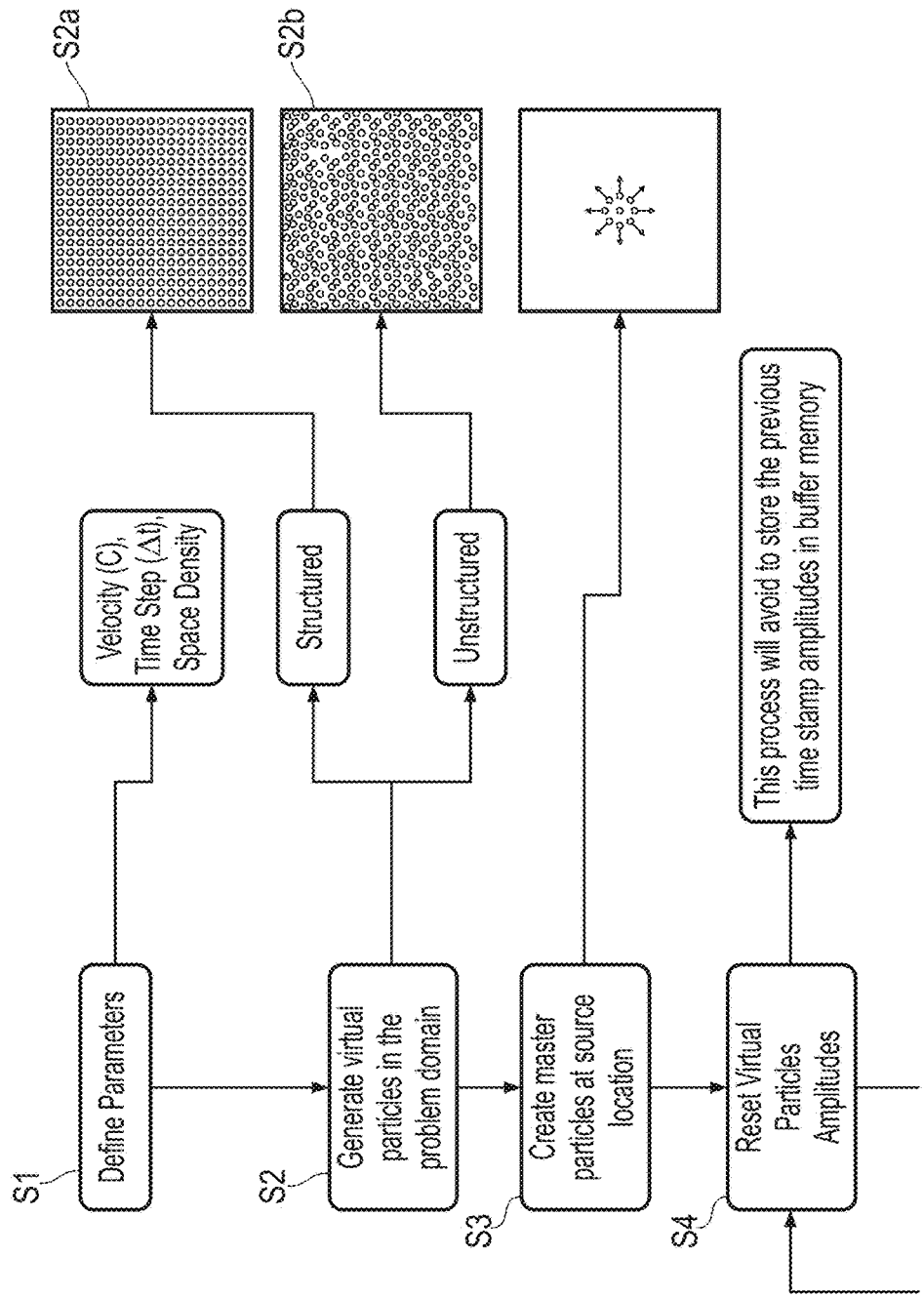
FIG. 10 shows a flow diagram of an optional visualisation step.
Figure 10:
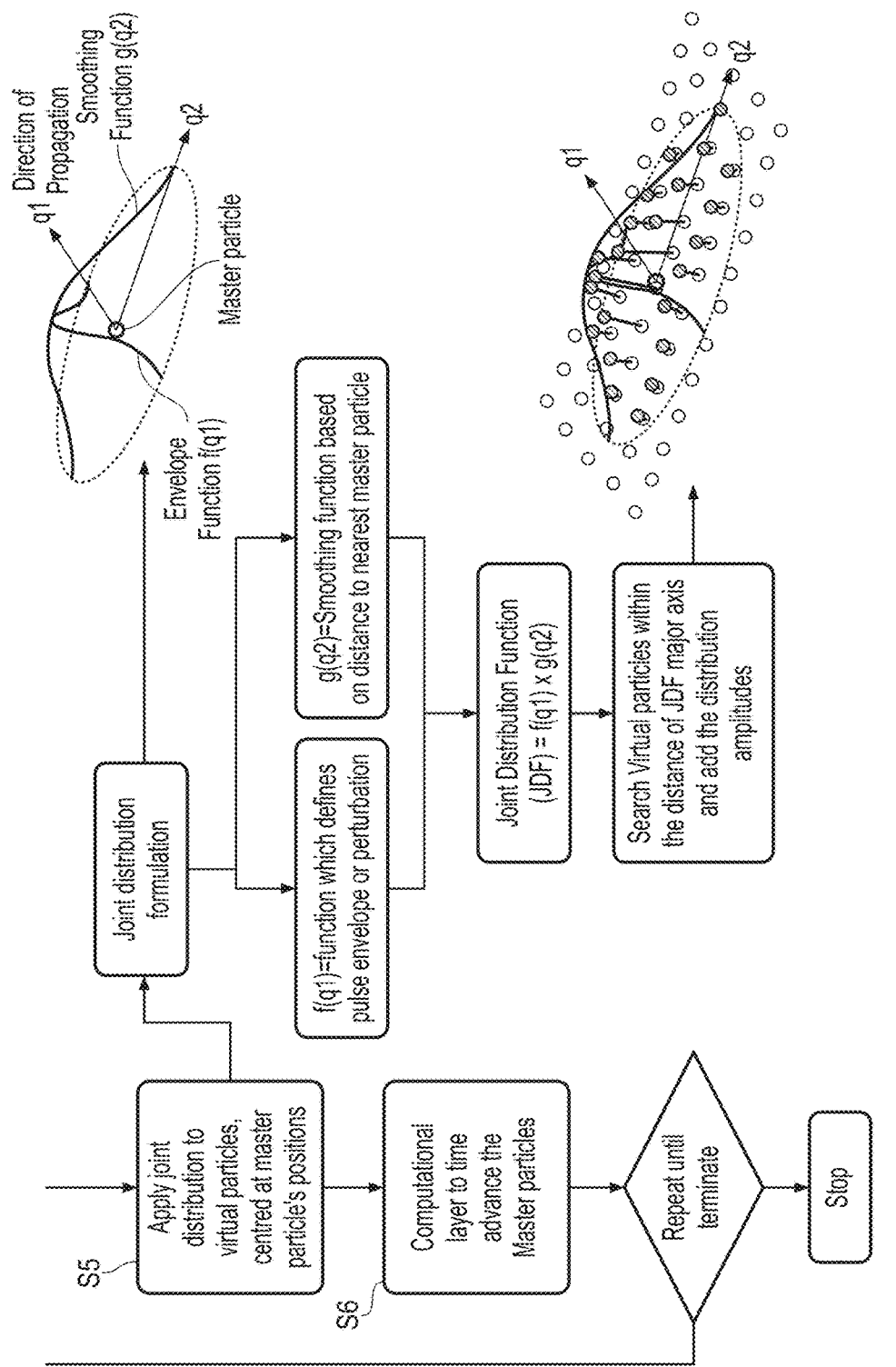
Figure 11:
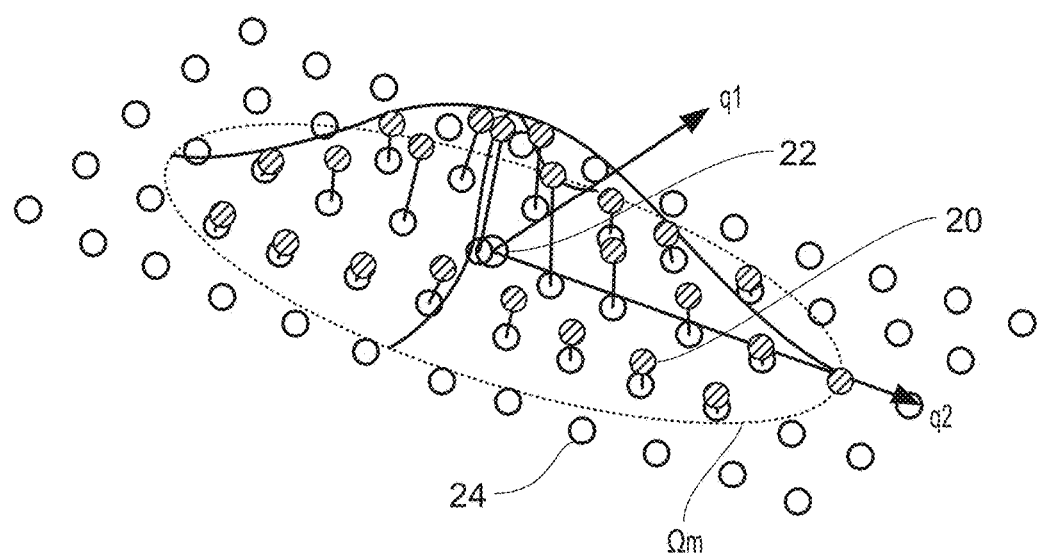
FIG. 11 details step S5 of the method steps of FIG. 10.

In order to better visualise the wavefront, and simulate features such as spreading and superposition of wavefronts, a virtual particle layer is provided in a fourth sub-step B4. FIGS. 10 and 11 shows how virtual particles 20 are used to achieve this.

In step S1, initial parameters of the master particles representative of the initial conditions of the wave to be modelled are defined. These parameters include the velocity of the energy wave in question in the simulated medium (for example, the speed of sound in the medium where the wave is a sound wave), as well as the initial amplitude of the wave, and the initial wavelength of the energy wave. Where the medium is anisotropic (i.e. the speed of sound is dependent on the direction of travel), this parameter may comprise a direction dependent function.

A plurality of spaced points in the form of virtual particles 20 are defined in a problem domain, i.e. within the original polygon, including the folded wavefront in step S2. The virtual particles 20 are provided in either a regular pattern, or in a randomly or pseudo-randomly generated irregular pattern. Each virtual particle 20 represents the magnitude of a desired field variable (such as material perturbation caused by the sound wave in the case of an ultrasonic sound wave) at the location within the problem domain of the respective virtual particle 20.

In step S3, the master particles are created. In step S4 the values of the virtual particles are reset. A supporting domain $\Omega_m$ is defined for each master particle. The supporting domain $\Omega_m$ defines a region on the problem domain in which the magnitude of the master particle 22 is to be distributed to the virtual particles 20. In the example shown in FIG. 11, the supporting domain comprises an ellipse having a first axis q1 extending in a direction of propagation of the master particle, and a second axis q2 extending in a direction normal to the direction of propagation of the master particle. The length of the first axis q1 could comprise the wavelength of the energy wave (as defined in step S1 or calculated in accordance with step S6, described below). In the case of ultrasonic waves having a high frequency, the first axis could comprise the pulse length of the wave. The second axis q2 comprises the distance between respective master particle and an adjacent master particle, as defined by the master particle spatial resolution defined in step S1 for the case of time step T=0.

In step S5, the magnitude $u_v$ of each of the virtual particles in the problem domain is calculated in accordance with the following formula:

$$u_v = \sum_{m=1}^{N} u_m f(q1) \times g(q2) \quad \text{(Formula 1)}$$

Where $v \in \Omega_m$

In formula 1, N is the total number of master particles within the domain of interest, $u_m$ is the magnitude of a respective master particle for the field variable of interest (as determined by the parameters set in step S1 for time t=0, or in step S6 as described below for subsequent time steps), $f(q1)$ is an envelope function relating the magnitude of the virtual particle to the distance from the respective master particle in the direction of propagation of the respective master particle (i.e. axis q1), and $g(q2)$ is a smoothing function relating the magnitude of the virtual particle to the distance from the respective master particle normal to the direction of propagation of the master particle (i.e. axis q2). The product of $f(q1)$ and $g(q2)$ is referred to hereafter as the "joint distribution function". The above is calculated where v is a member of (i.e. located within) a supporting domain $\Omega_m$ of a master particle.

The envelope function could comprise any of a Gaussian function, a linear smoothing function, and a moving average smoothing function. Essentially, the envelope function represents the distribution of wave intensity through its wavelength, which in mode cases is essentially a Gaussian distribution. In this example, where the energy wave comprises an ultrasonic wave, the envelope function f(q1) and smoothing function g(q2) could be of the form $$f(q1) = e^{\frac{(y_m - y_v)^2}{2 * \text{wavelength of pulse}^2}}$$

$$g(q2) = e^{\frac{(x_m - x_v)^2}{2 * \text{smoothing distance}^2}}$$

Where, master particles' co-ordinate $(x_m, y_m)$ and virtual particles' co-ordinate $(x_v, y_v)$ are measured with respect to moving frame (q1, q2) of respective master particle. FIG. 11 shows a worked example of calculated magnitudes for virtual particles 20 within the supporting domain $\Omega_m$ of a single master particle 22. In FIG. 4, the magnitude of the virtual particles is represented by the height of each particle above the plane of surrounding virtual particles 24, which lie outside the supporting region $\Omega_m$. as can be seen, the magnitude of the master particle 22 is distributed to the surrounding virtual particles 24 within the supporting region $\Omega_m$.

At a given time step, the joint distribution function is applied to the virtual particles 20 within the supporting region $\Omega_m$ for each master particle 22. As can be seen from FIG. 4, the magnitude of the virtual particles 20 at each location is a function of the product of the envelope function and the smoothing function for the location of each virtual particle 20. In addition to smoothing the wavefront, the above method allows the superposition of waves to be calculated for each time step, since in locations where the wavefront overlaps with other reflected wavefronts, more than one master particle 22 will be adjacent each virtual particle 20, and so the magnitude of the master particles will be added, effectively simulating superposition of reflected wavefronts.

There are a number of ways in which the field variables can be calculated. In one example, the field variables are calculated by taking into account the effects of advection, spreading, reflection/refraction.

FIGS. 9a to 9e show example simulations of wavefront propagation using the above method at time steps 2, 4, 6, 8 and 10 respectively for a simple, rectangular domain. The simulation can be seen to produce complex and highly accurate locations and intensity of the wavefront for an arbitrary time step.

The above described single domain method can be extended to accurately model a multiple domain scheme representative of an ultrasonic inspection process in accordance with the following modifications.

Figure 2:
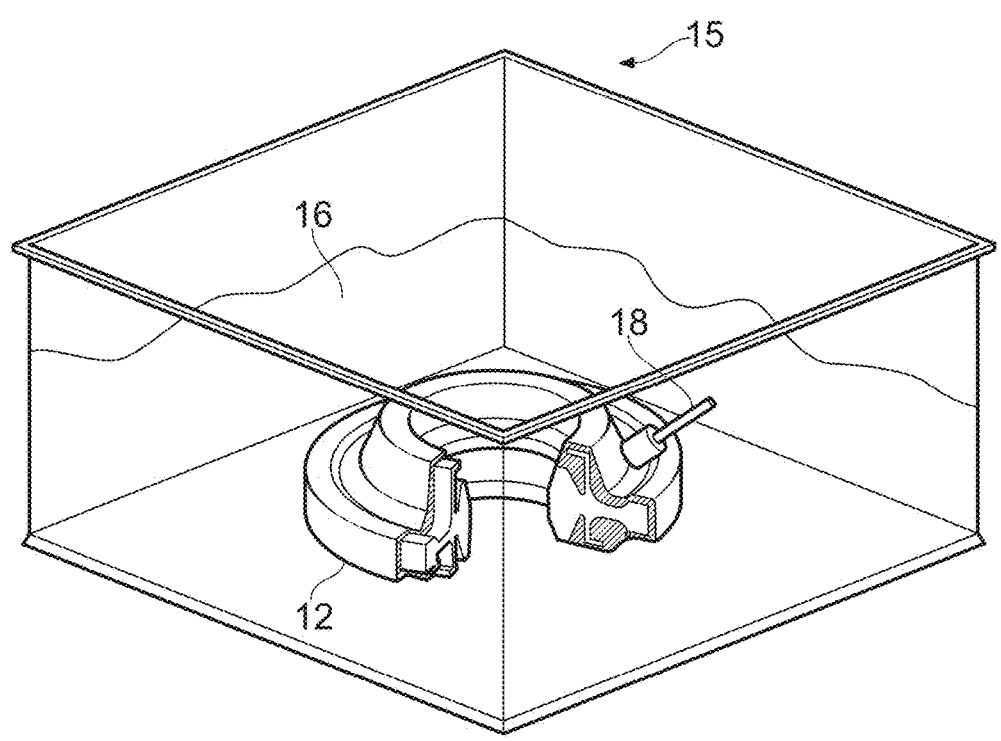
FIG. 2 shows an perspective view of an inspection arrangement.

In an ultrasonic inspection process, such as that carried out with the apparatus 15 shown in FIG. 2, the ultrasonic wave will generally propagate through at least two different media (namely water and nickel alloy in the case described above). Consequently, between being produced by the transducer, and the reflection being received by the transducer, the wave will undergo refraction at least twice, as well as being partly reflected by the interfaces between the media, in addition to the internal reflections within the media of interest. In order to accurately model the inspectability of the COS 12, these refractions and additional reflections must be taken into account.

In the single domain model illustrative above, all surfaces of the polygon D are considered to be entirely reflective, i.e. 100% of wave energy is reflected by the walls, with no energy being transmitted through the walls or attenuated by the walls. In this embodiment, four classes of polygon side are defined: fixed (R), interface (R, r), radiating (X) and transducer (M). In each case, waves approaching each side type are either reflected, refracted, terminated or measured respectively.

Fixed sides (R) behave in a similar manner to the single domain scheme, in which polygons are reflected in sub-step B2e. Under this regime, master particle locations within the reflected polygon and their direction of propagation are also reflected.

Figure 13A:
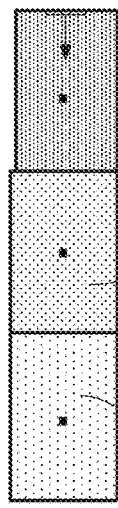
FIGS. 13a and 13b show origami maps $OM_1$, $OM_2$ for the domains $D_1$, $D_2$ of FIG. 12.

Radiating sides (X) do not reflect waves, and so these portions of the origami map are labelled "terminate origami space, and are ignored during the simulation phase, as shown in FIG. 13a. Consequently, master particles located in these regions are not reflected.

Master particles extending through the transducer side (M) are measured at the point where they cross the side to provide a simulation of a scan mode of the transducer 18.

The transducer side is chosen to reflect a desired location of the transducer in the ultrasonic inspection process.

The interface side (R, r) represents a boundary between the COS 12 and the transmission medium such as water 16. At this edge, the master particle is both reflected and refracted. During reflection, the master particles are treated in a similar manner to the master particles crossing the fixed sides (R). However, during the refraction simulation, new master particles are defined at the interface side (R, r). The relative amounts of energy (and so magnitudes) shared by each master particle (reflected and refracted) is parameterised in accordance with an estimated acoustic impedance between the two domains. The angle of propagation of the new master particles is calculated using Snell's law. Further diffractive points may also be added for concaves corners of the polygon.

Figure 12:
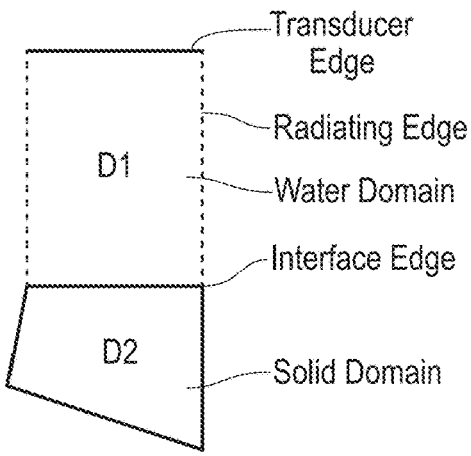
FIG. 12 shows a dual-domain region of interest.

FIG. 12 shows a worked example of the dual-domain model for a polygon $D_1$ representative of a water domain, bounded by a polygon $D_2$ representative of a COS 12 domain. An interface side (R, r) is defined by the interface between $D_1$ and $D_2$, a transducer side (M) is defined by a side opposite the interface side (R, r), fixed sides ($R_1$, $R_2$, $R_3$) are defined by the remaining sides of the polygon $D_2$, and radiating sides ($X_1$, $X_2$) are defined by the remaining sides of polygon $D_1$.

Figure 13B:
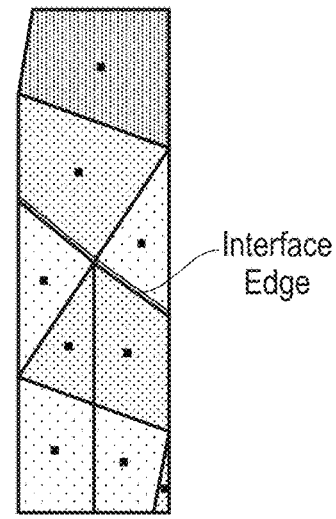

Origami maps $OM_1$ and $OM_2$ are defined for each polygon $D_1$, $D_2$ by carrying out sub-step B2 for each polygon $D_1$, $D_2$, as defined above, and are shown in FIGS. 13a and 13b.

These origami maps $OM_1$, $OM_2$ can then be used to simulate wave propagation through the apparatus 15. Simulation steps are carried out as described above, with the master particles being reflected at fixed sides (R), ignored at radiating sides (X), and measured at the transducer side (M). When a master particle crosses the interface side (R, r), a new master particle is created in the other origami map (i.e. where the master particle originated in $OM_1$, the new master particle is created in $OM_2$), and the simulation is continued in the other origami map.

Simulation results using the above described model have been found to accurately replicate experimental results for a large number of test articles. Consequently, the method is regarded as being highly successful. While other methods are known for simulating wave propagation through media are known, the present method is thought to have a high accuracy, while also having high computational efficiency compared to earlier methods.

The above described method can be used to determine the ultrasonic inspectability of a component as follows, and with reference to FIG. 14. A COS 12 is designed, and converted to a rectilinear form for inspectability testing. In this example, the inspectability of a second side $E_2$ of the component COS 12 from the first side $E_1$ is to be assessed. In practice, several simulated inspections may be made from different sides to determine whether the whole COS 12 inspectable. In some cases however, it may only be necessary to assess portions of the COS 12 for inspectability. As can be seen, to inspect each side, the transducer 18 is "indexed", i.e. moved parallel to the respective side ($E_1$ in this case) in steps of 1.2 mm, after each scan until the whole side $E_1$ is scanned at this resolution.

In a first step of assessing the inspectability of the COS 12, simulation parameters are set. In this example, the wave first travels through water prior to reaching side E, then travels through a titanium metal while travelling within the COS 12, between sides E and $E_2$. The speed of sound of each medium is set at 1.485 mm/μs in water, and 6.12 mm/μs in titanium. The ultrasonic frequency of the wave is set at 5 MHz, a water gap (i.e. the gap between the wavesource and side $E_1$) is set at 160 mm, and the index step size is set at 1.2 mm. A maximum wave propagation time is also defined, which represents the maximum time that the ultrasonic wave can propagate through the COS 12 before the wave is attenuated to such a degree that it can no longer be detected reliably by the transducer 18.

In a second step of assessing the inspectability of the COS 12, in the simulation, a wavesource is placed to one side $E_1$ of the component, spaced from the COS 12 by the water gap (160 mm in this example) at a first index step position. An origami map of the COS 12 is produced using the procedure described above.

Wave propagation through the COS 12 is then simulated using the origami map in accordance with the procedure described above. The wave propagation is time stepped, such that the wave propagation is assessed at each time step Δt, until either a wave reflected from the second side $E_2$ impinges on the transducer 18, or the maximum wave propagation time is reached. If a wave reflected from the second side $E_2$ impinges on the transducer 18 prior to the maximum wave propagation time, then the second side $E_2$ is deemed to be inspectable.

The above steps (origami map creation, wave propagation simulation) are then repeated for each index step, with the wave source location moved each time to simulated the movement of the transducer with each index step. If a wave reflected from the second side $E_2$ can be detected within the maximum wave propagation time for each index step, then side $E_2$ is regarded as being inspectable from the side $E_1$. This process may then be repeated for different side pairs, until the user is satisfied that all sides of interest are inspectable from accessible locations.

Figure 14:
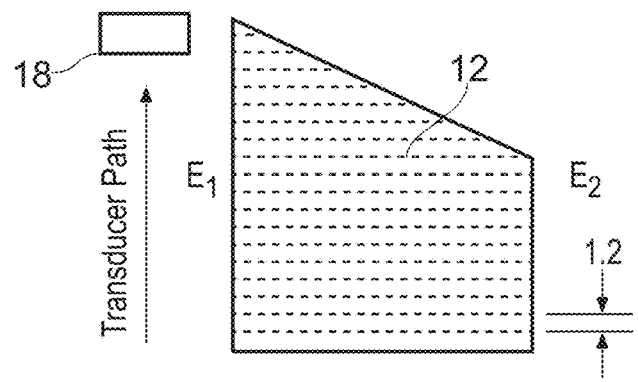
FIG. 14 shows a condition of supply geometry (COS) for testing.
Figure 15A:
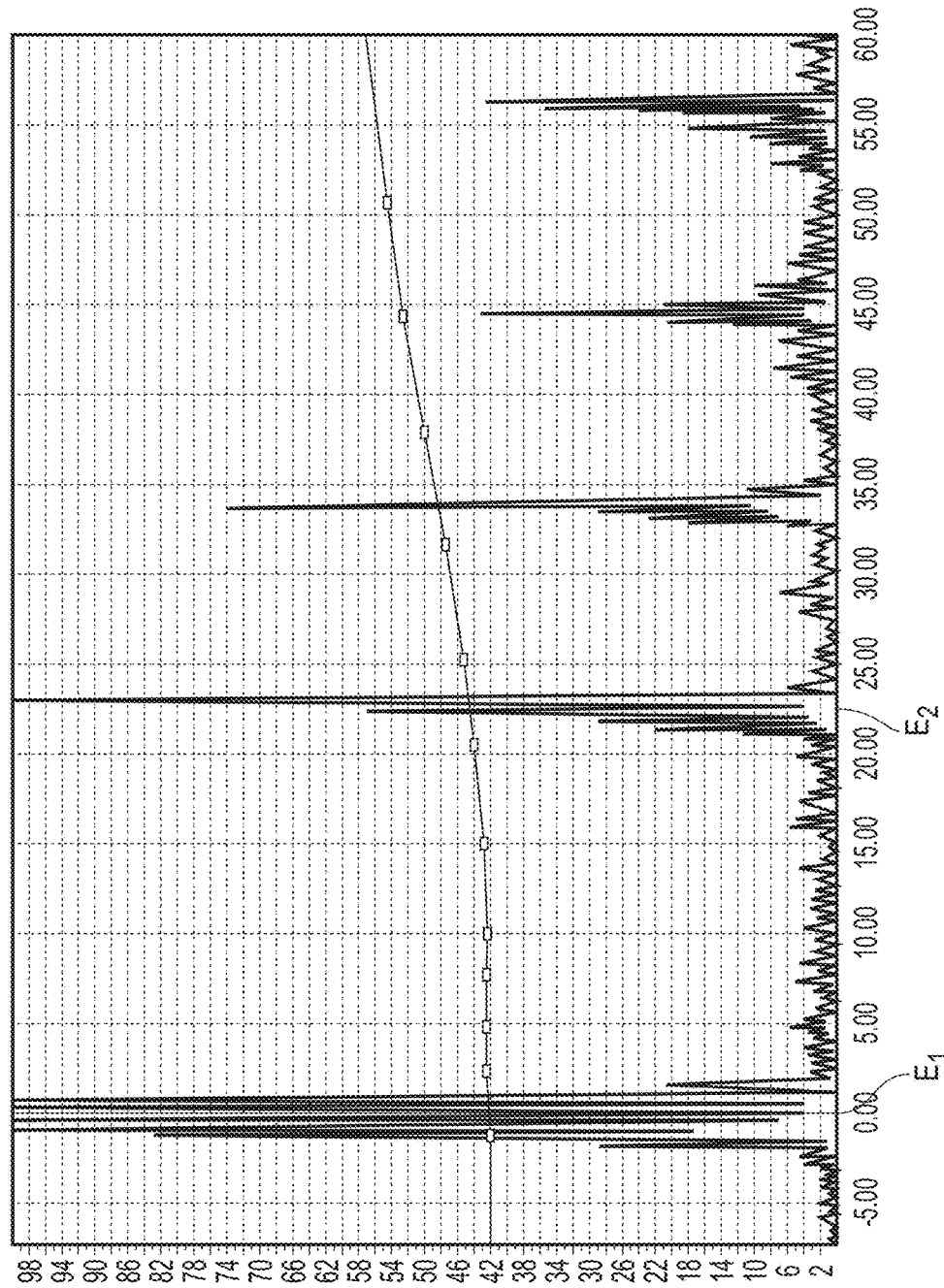
FIGS. 15a and 15b show simulated and experimental A-scan graphs respectively for the COS shown in FIG. 14.
Figure 15B:
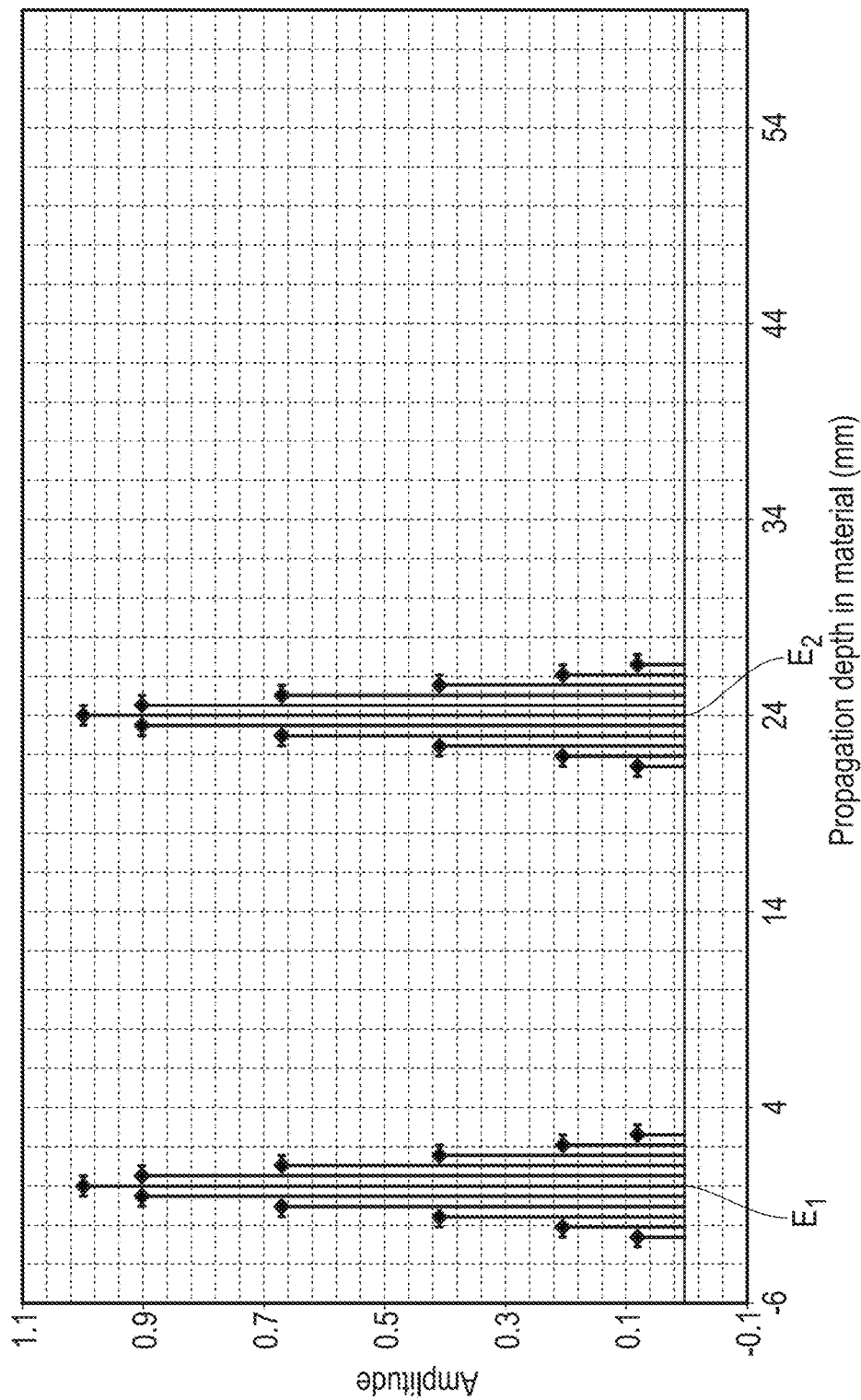

FIGS. 15a and 15b show a simulated and an experimental A-scan graph for the COS 12 shown in FIG. 14. As can be seen, two peaks can be observed in each graph, the positions of which are very similar in each case (confirming the accuracy of the simulation). A first peak corresponds with reflections from side $E_1$ being received by the transducer 18, and a second peak corresponds with reflections from side $E_2$ being received by the transducer 18. The time difference between these peaks represents the wave propagation time within the COS 12, and so this time difference is assessed to determine whether the time difference is less than the maximum time difference, and so inspectable.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

Aspects of any of the embodiments of the invention could be combined with aspects of other embodiments, where appropriate.

The invention claimed is:

1. A computer implemented method of determining an inspectability of a component by ultrasonic testing, the method comprising steps of:
   (1) defining: (i) a parent polygon representative of the component to be inspected, the parent polygon including one or more critical regions; (ii) an origin corresponding to a position of a wavesource within the parent polygon; (iii) a wavefront geometry of the wavesource; and (iv) a maximum wavefront extent;
   (2) determining one or more valid polygon sides of the parent polygon;
   (3) for each valid side of the parent polygon, defining a plurality of cutting lines extending from vertices of the valid sides to the maximum wavefront extent;
   (4) for each valid side of the parent polygon, reflecting the parent polygon about the respective valid side to define a child polygon;
   (5) discarding portions of each child polygon which lies beyond a cutting line from the respective valid side of the parent polygon;
   (6) redefining each child polygon as a parent polygon, and repeating steps (2) to (5) for each parent polygon until an area within the maximum wavefront extent is filled with polygons;
   (7) projecting onto the polygons within the maximum wavefront extent, a test wavefront having the wavefront geometry spaced from the origin by a specified distance;
   (8) reflecting the child polygons along the respective valid sides of the respective parent polygons to project the child polygons and test wavefront onto the original parent polygon, each respective valid side of the component is determined to be inspectable using a wavesource originating from the origin where a wavefront originating from the origin is determined to propagate back to the respective valid side through the one or more critical regions within a predetermined maximum propagation time;
   (9) upon determining that at least one side of the component is not inspectable by determining that a wavefront originating from the origin does not propagate back to a sensor, iteratively modifying the parent polygon and performing steps (1)-(8) until every side of the component is determined to be inspectable; and
   (10) indicating a final design of the component that is inspectable, and transmitting the indicated final design that is manufactured according to design matching the defined parent polygon such that the manufactured component is inspectable by ultrasonic testing.

2. The method according to claim 1, wherein the original parent polygon has a geometry representative of a nominal geometry of a workpiece to be inspected by ultrasonic testing.

3. The method according to claim 1, wherein the wavefront geometry includes one of a circular wavefront geometry and a spherical wavefront geometry.

4. The method according to claim 1, wherein the wavefront geometry includes one of a linear wavefront geometry and a planar wavefront geometry.

5. The method according to claim 1, wherein the step of defining the maximum extent of the wavefront of the predetermined time limit includes calculating a maximum distance (XR) of the wavefront from the origin at the predetermined time using the formula:

$$XR = cT$$

where c is a speed of propagation of the wave and T is a predetermined maximum wavefront propagation time.

6. The method according to claim 5, wherein:
   where the wavefront geometry is circular, the maximum extent includes a circle centered on the origin having a radius,
   where the wavefront geometry is spherical, the maximum extent includes a sphere centered on the origin having a radius,
   where the wavefront geometry is linear, the maximum extent includes a line located at a distance from the origin, and
   where the wavefront geometry is planar, the maximum extent includes a plane located at a distance from the origin.

7. The method according to claim 3, wherein the step of determining one or more valid polygon sides includes:
   for each side of the parent polygon, defining a pair of cutting lines extending from the origin to the vertices of the respective side, the respective polygon side being deemed not to be visible from the origin where either of the pair of cutting lines extends through a different side of the polygon prior to reaching the respective side of the respective parent polygon.

8. The method according to claim 4, wherein the step of determining one or more valid polygon sides includes:
   defining an initial wavefront vector,
   for each side of the parent polygon, projecting a cutting line from the vertices of each side in the direction of the initial wavefront vector, and
   determining whether the cutting lines extend toward the interior of the parent polygon, the respective polygon side being deemed not to be visible where either cutting line of the respective side extends toward the interior of the parent polygon.

9. The method according to claim 3, wherein the step of defining a plurality of cutting lines includes projecting respective cutting lines from the origin through the vertices of each valid side, to the wavefront maximum extent.

10. The method according to claim 4, wherein the step of defining a plurality of cutting lines includes projecting respective cutting lines from the vertices of the valid sides toward the wavefront maximum extent in the direction of the initial wavefront vector.

11. The method according to claim 1, wherein the step of defining the wavefront includes discretising the wave front into a plurality of spaced master particles, each master particle representing the position and field variables of a portion of the wavefront at the location of the respective master particle.

12. The method according to claim 11, wherein the step of projecting the wavefront onto the reflected polygons includes assigning each master particle to the respective polygon having the nearest centroid.

13. A non-transitory computer readable storage medium storing machine readable instructions causing one or more processors to perform steps of:
  (1) defining: (i) a parent polygon representative of the component to be inspected, the parent polygon including one or more critical regions; (ii) an origin corresponding to a position of a wavesource within the parent polygon; (iii) a wavefront geometry of the wavesource; and (iv) a maximum wavefront extent;
  (2) determining one or more valid polygon sides of the parent polygon;
  (3) for each valid side of the parent polygon, defining a plurality of cutting lines extending from vertices of the valid sides to the maximum wavefront extent;
  (4) for each valid side of the parent polygon, reflecting the parent polygon about the respective valid side to define a child polygon;
  (5) discarding portions of each child polygon which lies beyond a cutting line from the respective valid side of the parent polygon;
  (6) redefining each child polygon as a parent polygon, and repeating steps (2) to (5) for each parent polygon until an area within the maximum wavefront extent is filled with polygons;
  (7) projecting onto the polygons within the maximum wavefront extent, a test wavefront having the wavefront geometry spaced from the origin by a specified distance;
  (8) reflecting the child polygons along the respective valid sides of the respective parent polygons to project the child polygons and test wavefront onto the original parent polygon, each respective valid side of the component is determined to be inspectable using a wavesource originating from the origin where a wavefront originating from the origin is determined to propagate back to the respective valid side through the one or more critical regions within a predetermined maximum propagation time;
  (9) upon determining that at least one side of the component is not inspectable by determining that a wavefront originating from the origin does not propagate back to a sensor, iteratively modifying the parent polygon and performing steps (1)-(8) until every side of the component is determined to be inspectable; and
  (10) indicating a final design of the component that is inspectable, and transmitting the indicated final design that is manufactured according to design matching the defined parent polygon such that the manufactured component is inspectable by ultrasonic testing.

\* \* \* \* \*